United States Patent [19]
Jin et al.

[11] Patent Number: 5,730,898
[45] Date of Patent: Mar. 24, 1998

[54] THERMOTROPIC SIDE-CHAIN LIQUID CRYSTAL POLYMER AND FLCD EMPLOYING THE SAME AS AN ORIENTATION LAYER

[75] Inventors: Sung-ho Jin, Suwon; Shin Woong Kang, Seoul, both of Rep. of Korea

[73] Assignee: Samsung Display Devices Co., Ltd., Suwon, Rep. of Korea

[21] Appl. No.: 465,432

[22] Filed: Jun. 5, 1995

[30] Foreign Application Priority Data

Dec. 30, 1994 [KR] Rep. of Korea ............... 94-40135

[51] Int. Cl.$^6$ ............... C09K 19/52; C09K 19/32; C09K 19/12; G02F 1/1337
[52] U.S. Cl. ............... 252/299.01; 252/299.62; 252/299.66; 359/75; 359/103
[58] Field of Search ............... 252/299.01, 299.62, 252/299.66; 359/103, 75

[56] References Cited

U.S. PATENT DOCUMENTS

| | | | |
|---|---|---|---|
| 4,944,896 | 7/1990 | DeMartino et al. | 252/299.01 |
| 5,200,108 | 4/1993 | Yuasa et al. | 252/299.01 |

*Primary Examiner*—Shean C. Wu
*Attorney, Agent, or Firm*—Morgan & Finnegan, LLP

[57] ABSTRACT

A thermotropic side-chain liquid crystal polymer and a ferroelectric liquid crystal display employing the same as an orientation layer are provided. The thermotropic side-chain liquid crystal can be advantageously synthesized and is soluble in general organic solvents, thus exhibiting good processability. Further, the ferroelectric liquid crystal display employing the thermotropic side-chain liquid crystal polymer has a uniform orientation layer rarely having defects and good contrast ratio and memory characteristics.

2 Claims, 5 Drawing Sheets

THERMOTROPIC SIDE-CHAIN LIQUID CRYSTAL POLYMER AND FLCD EMPLOYING THE SAME AS AN ORIENTATION LAYER

BACKGROUND OF THE INVENTION

The present invention relates to a thermotropic side-chain liquid crystal polymer, and a ferroelectric liquid crystal display (LCD) having uniform orientation and good memory characteristics by employing the same as an orientation layer.

Liquid crystal has both the fluidity of liquid and the optical properties of crystal and is therefore classified as a material having mesophase between a liquid and a solid. Optical properties of the liquid crystal can be changed by either an electrical field or heat. Liquid crystal display using these properties of liquid crystal are one of the representatives of flat panel display devices, along with plasma displays and electroluminescence devices.

Super-twisted nematic (STN) and thin-film transistor twisted nematic (TFT-TN) LCDs are the main types commensurate with the current information society. They differ in terms of driving method and panel structure. In the STN-type LCDs, liquid crystal between the simple matrix-type upper and lower electrodes is driven passively with being twisted by 210°–270°. While, in the TFT-TN-type LCDs, each pixel is provided with a thin-film transistor to control the pixel, and 90° twisted liquid crystal provided between upper and lower electrodes is driven actively by the TFT. Though an STN-type LCD is advantageous in manufacture and cost, its response is slow and there is a limitation in pixel number, so that display characteristics thereof are poor. On the other hand, a TFT-TN-type LCD has good display characteristics but is difficult to manufacture and is expensive.

Meanwhile, ferroelectric liquid crystal displays (FLCDs) have certain advantages. That is, simple matrix-type passive driving is possible by using fast response characteristics and memory characteristics of the FLC, and a large high-definition display can be accomplished with a low price and without limitation in pixel number. A TFT-TN LCD is difficult to manufacture in sizes over 20" due to the production yield of the device, the prime cost and the limitation of panel size. However, the FLCD can be manufactured in sizes over 20". In addition, since the viewing angle is wide and memory characteristics are good, an image once input can be kept without continuous driving and so consumption of the electricity is very small. In the case of manufacturing reflection-type portable terminals using these characteristics of FLC, the display performance is better than an STN-type terminal of comparable quality level. Moreover, since the consumption of the electricity is 1/20 of that of the STN-type terminal, the operation time is longer with the limited battery capacity. Considering these points, research and development in the FLCD field is currently active as the potential LCD for the next generation.

The ferroelectric property of liquid crystal has become an interesting field since 1974, when it was reported that liquid crystal having a specific symmetric factor has ferroelectric properties. Then, in 1980, it was found that display devices having fast response characteristics and good memory characteristics could be manufactured by surface stabilizing the ferroelectric liquid crystal. Research into FLCDs has since continued with regard to application to large-screen high-definition displays such as portable terminals, office automation devices, work stations and wall televisions.

The orientation of ferroelectric liquid crystal using various polymers as the aligning material was studied since 1984, considering the relation between the characteristics of the aligning materials and orientation treatment. As a result, it was found that ferroelectric liquid crystal could be aligned better when using a thermoplastic polymer liquid crystal than when using a thermosetting polymer liquid crystal as an orientation layer.

When manufacturing liquid crystal panels using ferroelectric liquid crystal, one of the most important technique is the development of a material for uniform alignment of the liquid crystal so as to obtain good electro-optical properties and good memory characteristics.

In general, the physical property of liquid crystal varies according to the state of the molecular alignment. As a result, response characteristics of liquid crystal with respect to external factors such as an electric field are also considerably changed. Thus, it becomes an important technology to control the uniform orientation of the liquid crystal in manufacturing liquid crystal displays. Many studies have been vigorously conducted to this end.

The uniformmolecular alignment of the liquid crystals is difficult to obtain by merely injecting the liquid crystal between upper and lower substrates. Therefore, for uniform orientation, an orientation film is generally provided between the substrates.

As the orientation method for liquid crystal, the molecular alignment is controlled by oblique evaporation of inorganic materials (mainly, silicone oxide) without rubbing treatment. The method using inorganic material, however, is being considered only in laboratory scale because large scale production is difficult due to the spatial non-uniformity and the low productivity thereof is not suitable for mass production. Therefore, organic orientation layers obtained by coating an organic polymer, followed by rubbing with a piece of cloth are generally used. Among organic polymers, polyimides have been mainly used in consideration of the requirements for orientation layers, such as efficiency in mass production, orientation efficiency for liquid crystal molecules and resistance to unfavorable environment.

However, the typical polyimide orientation materials have several disadvantages.

First, since highly pure monomer and solvent are necessary to synthesize polyamic acids (PA) which are precursors of polyimides, synthesis is difficult and costly.

Second, the solvent N-methyl-2-pyrrolidone (NMP) is highly hygroscopic and the above polyamic acids are decomposed by water. Therefore, when PA is used or stored in an open system for a long period, its molecular weight decreases, thereby resulting in change in their physical properties.

Third, it is difficult to obtain a uniform and thin film of 600 Å or less.

Fourth, in the case of polyamic acids, siloxane groups are incorporated to a polymer backbone or a silane coupling agent for improving the adhesiveness to the substrate and a system added with a metal complex is used for regulating the contacting angle between liquid crystal and orientation film. Thus, uniform orientation control is hard to accomplish. Also, it is difficult to evaluate the affect of the interaction between molecular structures of liquid crystal and orientation agent on the molecular alignment, thereby making it difficult to select and design the liquid crystal and orientation agent efficiently.

Fifth, orientation characteristics of conventional orientation materials are liable to be changed by changes in device manufacturing conditions such as curing temperature or orientation conditions.

To develop an FLCD having good display characteristics, a technique for controlling the uniform orientation of liquid crystal is essential. Particularly, in the case of surface stabilized ferroelectric liquid crystal displays, since liquid crystal materials having a chiral smectic phase (SmC*) are used, if liquid crystal is injected in an isotropic phase and then the temperature is lowered, the liquid crystal becomes a smectic A phase having a layer structure perpendicular to the rubbing direction via a chiral nematic phase (N*) and is again changed into the chiral smectic phase so that the molecules within the layer are tilted at a specific angle with respect to the rubbing direction. At this time, as the gap between the smectic layers becomes reduced, bends in the smectic layers occur in order to compensate for the change of volume. This bent layer structure is called a chevron. Domains having different liquid crystal orientation are formed according to the directions of the bends. The non-uniform orientation is achieved where "zigzag," "hair-pin" or "mountain" defects are present on the boundary surface. As the result, the contrast ratio is lowered and a device of inferior bistability is obtained.

SUMMARY OF THE INVENTION

To solve the above described problems, it is an object of the present invention to provide a novel thermotropic side-chain liquid crystal polymer which overcomes the defects of the conventional polyimide.

It is another object of the present invention to provide a ferroelectric liquid crystal display having improved display characteristics and productivity, by controlling the liquid crystal orientation characteristics employing a thermotropic side-chain liquid crystal polymer as an orientation layer.

To accomplish the first object of the present invention, there is provided a thermotropic side-chain liquid crystal polymer represented as the following formula (I),

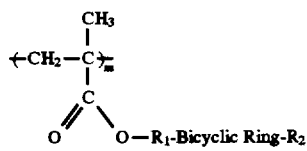

wherein $R_1$ is an alkoxy group, $R_2$ is an alkoxy group, halogen group or CN groups and m is an integer of 10–100.

Preferably, $R_1$ is $(CH_2)_nO$ or $(CH_2CH_2O)_n$, wherein n is an integer of 1–10.

Preferably, $R_2$ is an alkoxy group represented as $O(CH_2)_x CH_3$, wherein x is an integer of 1–6.

The bicyclic ring may be one of the aliphatic or aromatic bicyclic ring having the following structures.

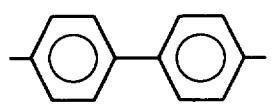

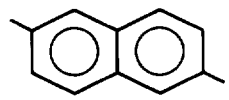

To accomplish another object of the present invention, there is provided a ferroelectric liquid crystal display comprising a pair of upper and lower substrates, transparent electrodes formed on each substrate, orientation layers formed on the transparent electrodes, and a ferroelectric liquid crystal layer injected between the orientation layers, characterized in that the orientation layer includes a thermotropic side-chain liquid crystal polymer represented as the following formula (I),

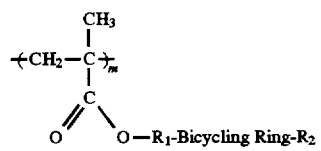

wherein $R_1$ is an alkoxy group, $R_2$ is an alkoxy group, halogen group or CN group, and m is an integer of 10–100.

Preferably, $R_1$ is $(CH_2)_nO$ or $(CH_2CH_2O)_n$, wherein n is an integer of 1–10.

Preferably, $R_2$ is an alkoxy group represented as $O(CH_2)_x CH_3$, wherein x is an integer of 1–6.

The bicyclic ring may be one of the aliphatic or aromatic bicyclic ring having the following structures.

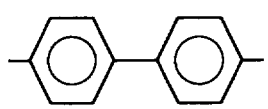

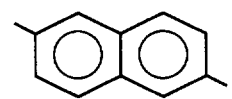

The thermotropic side-chain liquid crystal polymer of the formula (I) can be dissolved in common organic solvents. Particularly, a solution obtained by dissolving the polymer in cyclohexanone in a 2 wt % concentration is spin-coated on the substrate, to be formed into a thin film of 0.05–5 μm. An orientation layer manufactured by this method is a uniform layer having few pin holes or other defects, and is stable to oxygen in the air, humidity or chemicals and exhibits especially good adhesiveness to the substrate.

BRIEF DESCRIPTION OF THE DRAWINGS

The above objects and advantages of the present invention will become more apparent by describing in detail preferred embodiments thereof with reference to the attached drawings in which.

DETAILED DESCRIPTION OF THE INVENTION

Figure 1:
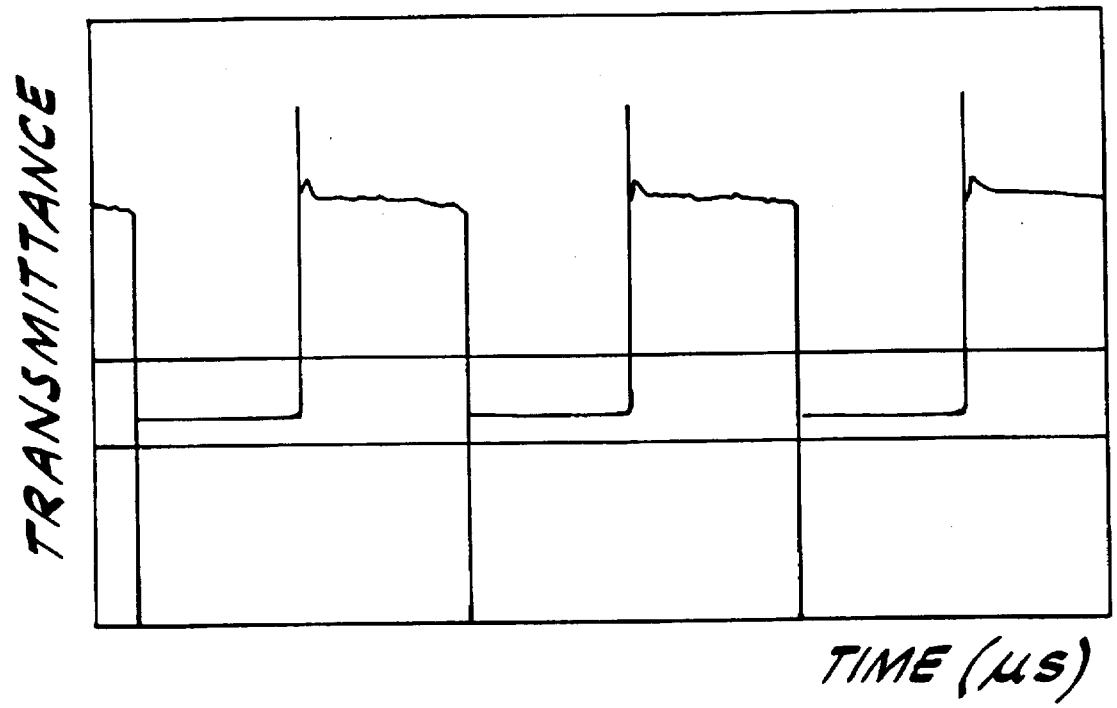
FIG. 1 is a graph illustrating electro-optical characteristics of a ferroelectric liquid crystal panel employing a thermotropic side-chain liquid crystal polymer (SCLCP-1) synthesized according to an embodiment of the present invention, in the liquid crystal orientation state under the electric field where a pulse height is ±20V, a pulse width is 50 μs, a frequency is 60 Hz.

The present invention will be described in detail below, while referring to the examples and attached drawings.

EXAMPLE 1

Preparation of 6-methoxy-6'-hexyloxy biphenyl methacrylate polymer (SCLCP-1)

1) Synthesis of 4-methoxy-4'-hydroxy biphenyl (1)

74 g (0.40 mol) of 4,4'-dihydroxybiphenyl was dissolved in an aqueous 10% NaOH solution and 50 g (0.4 mol) of dimethylsulfate was slowly dropped into this solution for a reaction. The solid formed with the progress of the reaction was separated by vacuum filtration, washed with 500 ml of aqueous 10% NaOH solution and placed into boiling distilled water. Insoluble precipitate was filtered off and the aqueous solution was acidified with 20% HCl solution to form a solid. The obtained solid was vacuum filtered and recrystallized with ethanol (m.p.: 163° C.; yield: 56%).

2) Synthesis of 4-methoxy-4'-hexyloxy biphenyl (2)

0.4 mol of the compound (1) was dissolved in a mixed solution of 150 ml of ethanol and an aqueous KOH solution (0.11 mol, 50 ml). To this mixture, 0.11 mol of 6-chloro-1-hexanol was slowly dropped and then kept for twenty hours for a reaction. After completion of the reaction, the reaction mixture was poured into 1 l of water to form a solid. The obtained solid was vacuum filtered, dried and recrystallized with 300 ml of ethanol (m.p.: 134°–136° C.; yield: 75%).

3) Synthesis of 6-methoxy-6'-hexyloxy biphenyl methacrylate (3)

$3.5 \times 10^{-3}$ mol of the compound (2) was dissolved in 50 ml of THF and 1 ml of triethylamine ($7 \times 10^{-3}$ mol). The solution was cooled to 0° C. and 0.5 ml ($5 \times 10^{-3}$ mol) of methacryloyl chloride was slowly dropped into this solution. The mixture was reacted for 24 hours at an ambient temperature and the reaction mixture was poured into 200 ml of water to form a solid. The obtained solid was vacuum filtered, dried and recrystallized with 70 ml of ethanol (yield: 79%).

4) Synthesis of 6-methoxy-6'-hexyloxy biphenyl methacrylate polymer (SCLCP-1)

1 g of the compound (3) was dissolved in 10 ml of 1,4-dioxane and 0.01 g (1 wt %) of AIBN (azobisisobutyronitrile) initiator for radical polymerization was injected to this solution under vacuum. After this, the polymerization reaction proceeded for 24 hours at 60° C. After completion of the polymerization, the reaction mixture was poured into 100 ml of methanol to form a precipitate, and the precipitate was vacuum filtered and dried. Synthetic yield was 80%, the number-average molecular weight was 14,800 and the molecular weight distribution was 2.7. The structure of the synthesized side-chain liquid crystal polymer (SCLQP-1) was confirmed by $^1$H-NMR, $^{13}$C-NMR and FT-IR. Physical properties thereof were observed using a DSC, an polarizing microscope, etc. Various physical properties are illustrated in Table 2.

EXAMPLE 2

Preparation of 6-cyano-6'-hexyloxy biphenyl methacrylate polymer (SCLQP-2)

Intermediate products, 4-cyano-4'-hexyloxybiphenyl compound (2') and 6'-cyano-6-hexyloxy biphenyl methacrylate compound (3') were synthesized by the same method for synthesizing the compounds (2) and (3) in example 1 using 4'-cyano-4-hydroxybiphenyl (1') as a starting material. 6-cyano-6'-hexyloxy biphenyl methacrylate polymer (SCLCP-2) was obtained by the same method for synthesizing the compound (3) in example 1. Various physical properties of this polymer were examined and are illustrated in Table 2.

EXAMPLE 3

Manufacture of experimental cell and injection of liquid crystal

1) Manufacture of experimental cell

Glass substrates were cleaned and transparent electrodes were patterned using photoresist. Next, orientation layers were coated on the electrode using RN-715 (Nissan Chemical) and liquid crystal polymer as illustrated in Table 1. Rubbing treatment is performed by a rubbing equipment wrapped with rayon fabric.

After rubbing treatment, a sealant was screen printed on the periphery (150 μm) of one substrate and heated to 80° C. for fifteen minutes to remove the solvent. The sealant was printed in a square shape, while leaving about 5–10 mm for injection of the liquid crystal. 1.5 μm spherical spacers were dispersed on the other substrate. The two substrates were then assembled and the liquid crystal panel was manufactured by pressing and heating at a constant pressure and temperature sufficient to cure the printed binder.

2) Filling of liquid crystal and evaluation of characteristics

Since the isotropic temperature of ferroelectric liquid crystal is higher than ambient temperature, unlike common liquid crystal, liquid crystal filling equipment provided with a heating device was used for heating during liquid crystal injection. The filling of the liquid crystal was accomplished by the pressure difference between atmospheric pressure and the internal vacuum ($1 \times 10^{-2}$) of the panel. Here, the liquid crystal employed was Felix-T250 (Hoechst). Since the isotropic temperature of the liquid crystal is 85° C., the injection was carried out at 90° C. For reference, the thermal properties of the Felix-T250 liquid crystal are as follows.

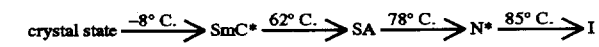

$$\text{crystal state} \xrightarrow{-8°\text{C.}} \text{SmC*} \xrightarrow{62°\text{C.}} \text{SA} \xrightarrow{78°\text{C.}} \text{N*} \xrightarrow{85°\text{C.}} \text{I}$$

Equipment used for evaluation of the characteristics were polarizing microscope for observing the alignment state of the ferroelectric liquid crystal and equipment for detecting electro-optical characteristics.

Figure 2:
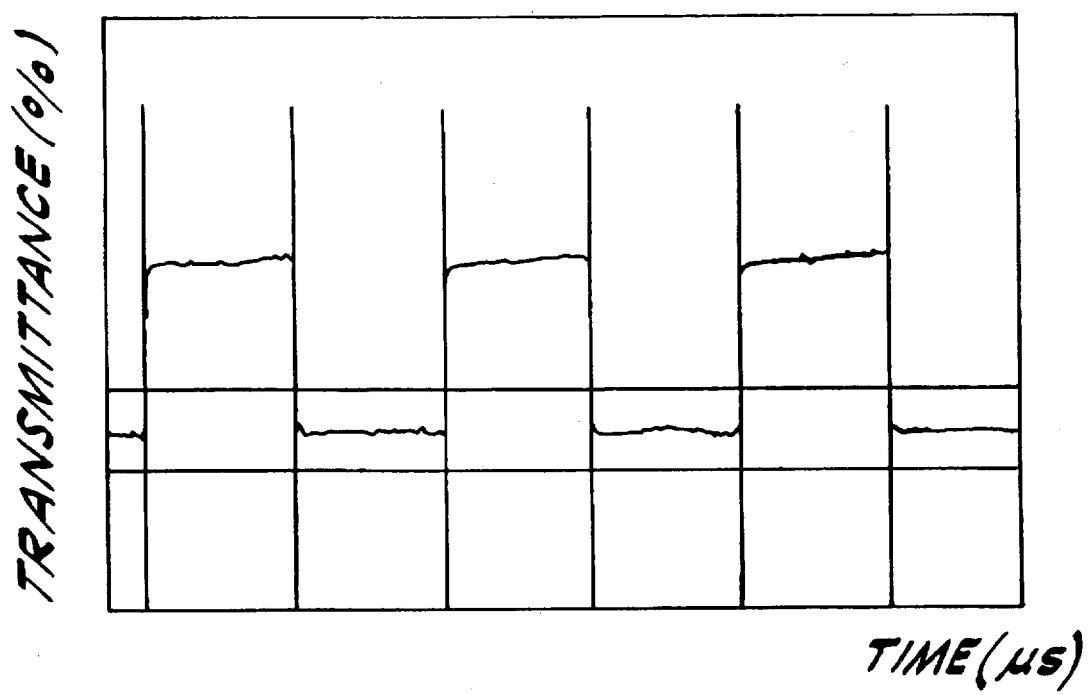
FIG. 2 is a graph illustrating electro-optical characteristics of a ferroelectric liquid crystal panel employing a thermotropic side-chain liquid crystal polymer (SCLCP-2) manufactured according to another embodiment of the present invention, in the liquid crystal orientation state under the electric field where pulse height is ±20V, pulse width is 50 μs, frequency is 60 Hz.

FIGS. 1 and 2 illustrate the bistability of ferroelectric liquid crystal cells employing SCLCP-1 and SCLCP-2 as the orientation layers, respectively.

Figure 3:
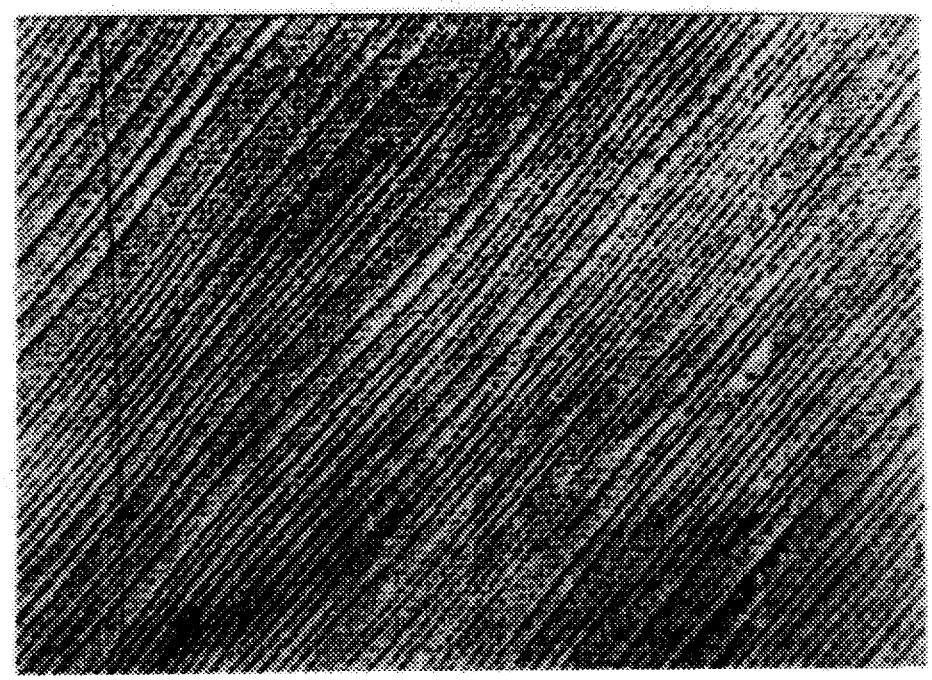
FIG. 3 is a diagram illustrating the orientation state of the liquid crystal of a ferroelectric liquid crystal panel manufactured by using thermotropic side-chain liquid crystal polymer (SCLCP-1) according to an embodiment of the present invention.
Figure 4:
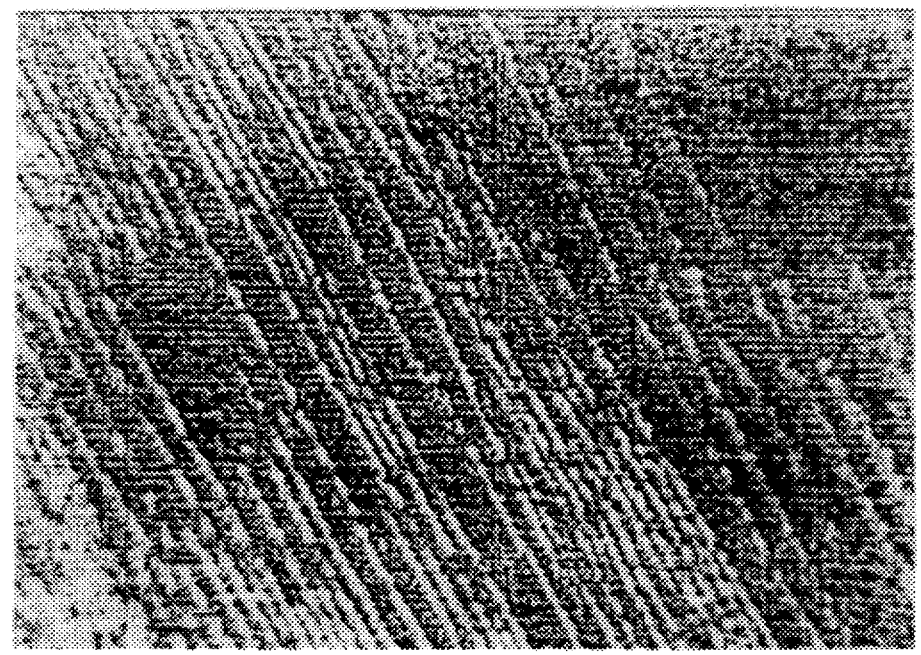
FIG. 4 is a diagram illustrating the orientation state of the liquid crystal of a ferroelectric liquid crystal panel manufactured by using thermotropic side-chain liquid crystal polymer (SCLCP-2) according to another embodiment of the present invention.

FIGS. 3 and 4 illustrate the liquid crystal orientation states of ferroelectric liquid crystal cells employing SCLCP-1 and SCLCP-2 as the orientation layers, respectively.

COMPARATIVE EXAMPLE 1

An LC cell was manufactured using RN-715 (Nissan Chemical) as an orientation layer for comparison and electro-optical characteristics thereof were examined.

RN-715 was diluted using a mixed solution of 1-methyl-2-pyrrolidone (NMP) and butyl cellosolve (80:20 by weight) to a 3 wt % concentration. The solution was spin coated on the electrode at 3000 rpm for twenty seconds, pre-dried at 80° C. for fifteen minutes and baked at 260° C. for thirty minutes. Detailed conditions on orientation treatment are illustrated in Table 1 along with those of the thermotropic side chain liquid crystal polymer of the present invention.

TABLE 1

| | conditions for coating of orientation material and thermal treatment | | | |
|---|---|---|---|---|
| orientation material | concentration/ solvent | coating rpm | curing (temp./duration) | orientation layer thickness |
| RN-715 | 1–3 wt %/ NMP(80), BuC(20) | 3000– 4000 | 80° C./15 min 260° C./30 min | 600–1000Å |
| SCLCP-1 SCLCP-2 | 2 wt %/ cyclohexanone | 3000 | 110° C./10 min | 0.05–5 μm |

After rubbing, an empty cell was manufactured by the same method described in example 3 and it was filled with Felix-T250 liquid crystal. Then, it was thermally and electrically stabilized to examine electro-optical characteristics.

Figure 5:
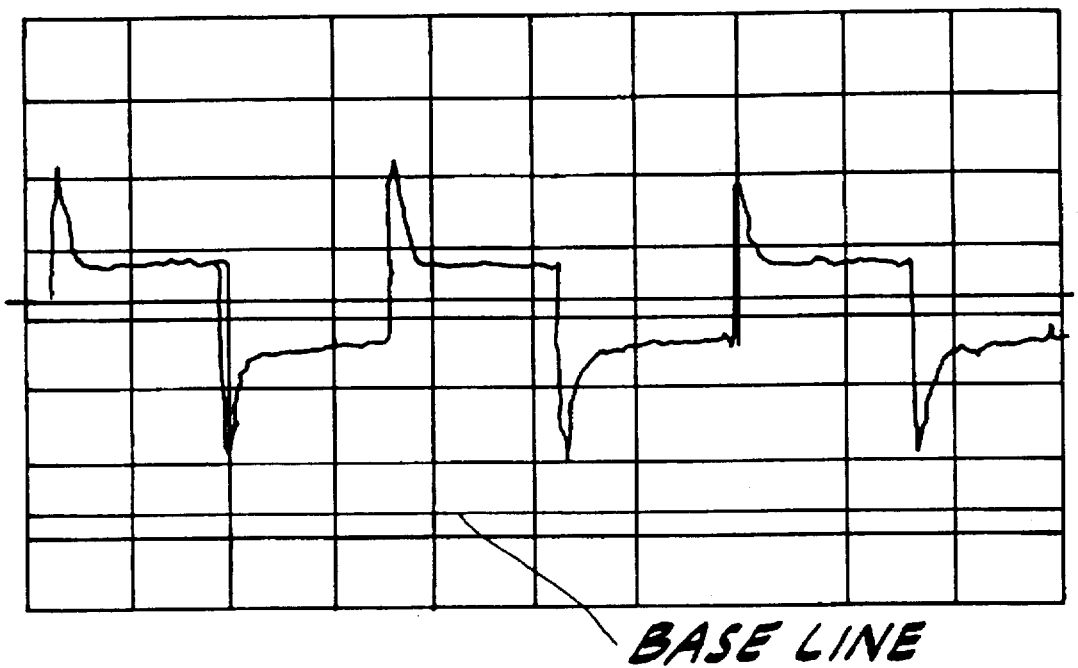
FIG. 5 illustrates the electro-optical characteristics of a ferroelectric liquid crystal panel manufactured according to a comparative example of the present invention.
Figure 6:
FIG. 6 illustrates the orientation state of the liquid crystal of a ferroelectric liquid crystal panel manufactured according to the comparative example of the present invention.

The results are illustrated in FIGS. 5 and 6 and Table 2. Here, FIG. 5 illustrates electro-optical characteristics of a ferroelectric liquid crystal panel according to the comparative example of the present invention in the liquid crystal orientation state under an electric field with a pulse height of ±20V, a pulse width of 50 μs and a frequency of 60 Hz. FIG. 6 illustrates the liquid crystal orientation state of a ferroelectric liquid crystal panel according to the comparative example. Also, the Table 2 shows characteristics of FLCDS according to orientation materials.

TABLE 2

| characteristics according to the orientation material | | | |
|---|---|---|---|
| orientation material | contrast ratio | $t_R$ (μm) | phase transition temperature (°C.) |
| RN-715 | 5/1 | 160 | |
| SCLCP-1 | 11/1 | 157 | K 119 S 136 i |
| SCLCP-2 | 7/1 | 144 | g 59 N 112 i |

From the above results, it can be seen that the thermotropic side-chain liquid crystal polymer of the present invention is good in solvent applicability and processability.

In conclusion, the liquid crystal orientation state obtained by the thermotropic side-chain liquid crystal polymer of the present invention is very uniform. Furthermore, good contrast ratio and memory characteristics and better processability can be implemented.

The following effects can be obtained by applying the new thermotropic side-chain liquid crystal polymer in the present invention to FLCD technology.

First, synthesis of the orientation material is simple and economic.

Second, the material can be dissolved in common organic solvents such as chloroform or THF and is stable against humidity. Thus, decomposition does not occur even in humid conditions and long-term stability can be achieved. Also, physical properties thereof rarely change.

Third, liquid crystal derivatives of the side chain can be aligned in a predetermined direction by thermal annealing, and ferroelectric liquid crystal compounds are aligned along the side-chain liquid crystal polymer of the orientation layer. Accordingly, the better orientation characteristics can be obtained than by the conventional PI orientation layer.

Fourth, the material shows good light transmittance and environmental resistance properties, a high adhesiveness to the substrate, the ability to form a uniform thin film, stability to chemicals, and good orientation characteristics by rubbing.

Fifth, a thin film having few pinholes or other defects and good orientation characteristics by rubbing can be achieved. Accordingly, an FLCD having a good contrast ratio and memory characteristics can be manufactured.

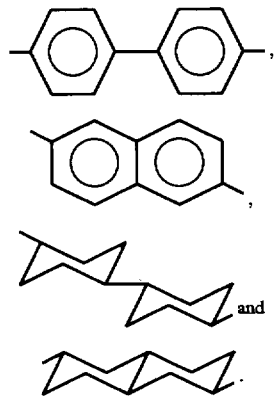

What is claimed is:

1. A ferroelectric liquid crystal display comprising a pair of upper and lower substrates, transparent electrodes formed on said each substrate, orientation layers formed on said transparent electrodes, and a ferroelectric liquid crystal injected between said orientation layers, characterized in that said orientation layer includes a thermotropic side-chain liquid crystal polymer represented as the following formula (I),

wherein $R_1$ is $(CH_2)_nO$, where n is an integer of 1–10, $R_2$ is a methoxy group, and m is an integer of 10–100.

2. A ferroelectric liquid crystal display as claimed in wherein said bicyclic ring is selected from the group consisting of the following structures